US009861725B2

(12) United States Patent
Vikinge et al.

(10) Patent No.: US 9,861,725 B2
(45) Date of Patent: Jan. 9, 2018

(54) MULTILAYER PROTEIN FILMS, METHODS OF MAKING, AND DRUG DELIVERY DEVICES AND BIOMEDICAL IMPLANTS EMPLOYING THE FILMS

(75) Inventors: Ella Cathrine Vikinge, Brokind (SE); Elin Engström, Hisings Backa (SE); Henrik Aronsson, Ljungsbro (SE); Oskar Axelsson, Höör (SE)

(73) Assignee: ADDBIO AB, Linkoping (SE)

( * ) Notice: Subject to any disclaimer, the term of this patent is extended or adjusted under 35 U.S.C. 154(b) by 0 days.

(21) Appl. No.: 13/319,327

(22) PCT Filed: May 24, 2010

(86) PCT No.: PCT/SE2010/050560
§ 371 (c)(1),
(2), (4) Date: Jan. 20, 2012

(87) PCT Pub. No.: WO2010/138062
PCT Pub. Date: Dec. 2, 2010

(65) Prior Publication Data
US 2012/0114731 A1  May 10, 2012

Related U.S. Application Data

(60) Provisional application No. 61/181,884, filed on May 28, 2009.

(51) Int. Cl.
*A61L 27/54* (2006.01)
*A61L 27/34* (2006.01)
*A61C 8/00* (2006.01)

(52) U.S. Cl.
CPC ............. *A61L 27/54* (2013.01); *A61L 27/34* (2013.01); *A61C 8/0013* (2013.01); *A61L 2300/112* (2013.01); *A61L 2300/252* (2013.01); *A61L 2300/406* (2013.01); *A61L 2300/422* (2013.01); *A61L 2300/608* (2013.01); *Y10T 428/273* (2015.01)

(58) Field of Classification Search
CPC .... A61L 27/54; A61L 27/34; A61L 2300/112; A61L 2300/252; A61L 2300/406; A61L 2300/422; A61L 2300/608; A61C 8/0013; Y10T 428/273
See application file for complete search history.

(56) References Cited

U.S. PATENT DOCUMENTS

| | | | |
|---|---|---|---|
| 4,531,916 A * | 7/1985 | Scantlebury | A61C 8/00 433/173 |
| 5,272,074 A * | 12/1993 | Rubens | 435/180 |
| 2002/0197467 A1* | 12/2002 | Johnson | C08J 7/12 428/333 |
| 2002/0198590 A1 | 12/2002 | Ung-Chhun | |
| 2004/0109937 A1 | 6/2004 | Jennissen et al. | |
| 2005/0049693 A1* | 3/2005 | Walker | 623/1.42 |
| 2006/0002970 A1 | 1/2006 | Aspenberg et al. | |
| 2006/0003917 A1 | 1/2006 | Aspenberg et al. | |
| 2009/0181161 A1 | 7/2009 | Jui et al. | |

FOREIGN PATENT DOCUMENTS

| | | |
|---|---|---|
| CN | 1871038 A | 11/2006 |
| EP | 1058343 A1 * | 2/2005 |
| EP | 1674116 A2 | 6/2006 |
| JP | 59-67965 A | 4/1984 |
| JP | 6-305983 A | 11/1994 |
| JP | 2004-65087 A | 3/2004 |
| JP | 2007-131638 A | 5/2007 |
| JP | 2007-533345 A | 11/2007 |
| JP | 2008-249465 A | 10/2008 |
| JP | 2009-67669 A | 4/2009 |
| WO | 1993/25246 A1 | 12/1993 |
| WO | 2001/56628 A1 | 8/2001 |
| WO | 2001/87267 A1 | 11/2001 |
| WO | 2003/043673 A1 | 5/2003 |
| WO | 2005/018699 A1 | 3/2005 |
| WO | 2005/079879 A1 | 9/2005 |
| WO | 2007/016524 A2 | 2/2007 |
| WO | WO-2007/048264 A1 * | 5/2007 |
| WO | 2007/128378 A1 | 11/2007 |
| WO | 2008/105732 A1 | 9/2008 |

OTHER PUBLICATIONS

Bai et al., Fibrinogen adsorption onto 316L stainless steel, Nitinol and titanium, Feb. 7, 2009, Surface Science, vol. 603, pp. 839-846.*
International Search Report and Written Opinion received for PCT Patent Application No. PCT/SE2010/050560, dated Sep. 16, 2010, 18 pages.
International Preliminary Report on Patentability received for PCT Patent Application No. PCT/SE2010/050560, dated Dec. 8, 2011, 13 pages.
Benesch et al., "The Determination of Thickness and Surface Mass Density of Mesothick Immunoprecipitate Layers by Null Ellipsometry and Protein 125Iodine Labeling", Journal of Colloid and Interface Science, vol. 249, 2002, pp. 84-90.
Cacciafesta et al., "Human Plasma Fibrinogen Adsorption on Ultraflat Titanium Oxide Surfaces Studied with Atomic Force Microscopy", Langmuir, vol. 16, 2000, pp. 8167-8175.
Cai et al. "Does the nanometre scale topography of titanium influence protein adsorption and cell proliferation?", Colloids and Surfaces B: Biointerfaces, vol. 49, Issue No. 2, 2006, pp. 136-144.
de Feijter et al., "Ellipsometry as a Tool to Study the Adsorption Behavior of Synthetic and Biopolymers at the Air-Water Interface", Biopolymers, vol. 17, 1978, pp. 1759-1772.
Ratner et al., "Biomaterials Science: An Introduction to Materials in Medicine", 2nd Edition, Elsevier Academic Press, 2004, 245 page.
Sogawa et al., "Use of Fluorescamine-Labeled Casein as a Substrate for Assay of Proteinases1", Journal of Biochemistry, vol. 83, No. 6, 1978, pp. 1783-1787.

(Continued)

*Primary Examiner* — Ali Soroush
(74) *Attorney, Agent, or Firm* — Morrison & Foerster LLP

(57) ABSTRACT

A multilayer protein film has a mass of greater than 0.5 µg/cm² and consists essentially of protein. A drug delivery device comprises the multilayer protein film onto which a pharmaceutically active agent can be loaded. A biomedical implant comprises an implant substrate and the multilayer protein film on at least a portion of the implant substrate surface. A method of making a multilayer protein film having a mass of greater than 0.5 µg/cm² comprises contacting a substrate with a protein solution at a temperature of from about 30° C. to about 95° C, wherein a multilayer protein film having a mass of greater than 0.5 µg/cm² is formed on the substrate.

8 Claims, No Drawings

(56) References Cited

OTHER PUBLICATIONS

Tengvall et al., "Preparation of multilayer plasma protein films on silicon by EDC/NHS coupling chemistry", Colloids and Surfaces B: Biointerfaces, vol. 28, 2003, pp. 261-272.
Udenfriend et al., "Fluorescamine: A Reagent for Assay of Amino Acids, Peptides, Proteins, and Primary Amines in the Picomole Range", Science, vol. 178, Nov. 24, 1972, pp. 871-872.
Office Action received for Chinese Patent Application No. 201080022732.0, dated Jun. 18, 2013, 18 pages (10 pages of English Translation.
Extended European Search Report received for European Patent Application No. 10780883.4, dated May 23, 2014, 8 pages.
Office Action received for Chinese Patent Application No. 201080022732.0, dated Jun. 4, 2014, 28 pages (19 pages of English translation.)
Office Action Received for Japanese Patent Application No. 2012-513013, dated Aug. 11, 2014, 9 pgaes (5 pages of English Translation).
Office Action Received for Japanese Patent Application No. 2012-513013, dated Apr. 20, 2015, 10 pages (5 pages of English Translation).

* cited by examiner

MULTILAYER PROTEIN FILMS, METHODS OF MAKING, AND DRUG DELIVERY DEVICES AND BIOMEDICAL IMPLANTS EMPLOYING THE FILMS

CROSS REFERENCE TO RELATED APPLICATIONS

This is a U.S. National Phase patent application of PCT/SE2010/050560, filed May 24, 2010, which claims priority to U.S. Provisional Patent Application No. 61/181,884, filed May 28, 2009, each of which is hereby incorporated by reference in the present disclosure in its entirety.

FIELD OF THE INVENTION

The present invention is directed to multilayer protein films and to methods of making multilayer protein films. The present invention is also directed to drug delivery devices comprising a multilayer protein film loaded with a pharmaceutically active agent and to biomedical implants comprising an implant substrate and a multilayer protein film on at least a portion of the implant substrate surface.

BACKGROUND OF THE INVENTION

There is a continuing need for improving biomedical implants and for improving the biocompatibility of biomedical implants upon implantation into an organism, i.e., the body. It is known that characteristics of the implant surface are strongly associated with the early events on the surface after implantation and these early events are important in determining device compatibility. It is believed that the composition, sequence, and other characteristics of proteins binding to an implant surface during the first seconds after introduction in to the organism will determine the events on a longer time scale and, ultimately, contribute to the degree of implant biocompatibility. Also, the properties of an implant surface affect the state of proteins associating with the surface, which also impacts subsequent interactions with the organism.

Typically, proteins form a monolayer on a surface in contact with the protein. See, for example, *Biomaterials Science, An Introduction to Materials in Medicine*, $2^{nd}$ Edition, B. Ratner et al, Editors, Elsevier Academic Press (2004), p. 245, Table 1. A monolayer typically has a thickness of 2-4 nm when measured with null ellipsometry. According to de Feijter et al, "Ellipsometry as a tool to study the adsorption of synthetic and biopolymers at the air-water interface," *Biopolymers*, 17:1759-1801 (1978), the monolayer thickness is converted to mass as 1 nm=0.12 µg/cm$^2$. Accordingly, a protein monolayer on a planar surface is typically less than 0.5 µg/cm$^2$, and often in the interval 0.2-0.5 µg/cm$^2$. Ellipsometry is often used to study multilayers as well, but is not as accurate when used in multilayer applications as shown by Benesch et al, "The determination of thickness and surface mass density of mesothick immunoprecipitate layers by null ellipsometry and protein $^{125}$iodine labeling," *Journal of Colloid and Interface Science*, 249:84-90 (2002). Also, ellipsometry can only be used on planar surfaces, and not on surfaces with a non-planar topography, which is often the case with implants. For these two reasons, protein mass per surface area is used to characterize multilayer dimension within this disclosure. Additionally, it is important to note that a device with macroscopic surface area of X may have a microscopic surface area, or nanosurface of area 10 or 100 times X, and the mass of a monolayer on a device may therefore seem much greater than a monolayer on a planar surface, due to topography and structure.

Generally, to form multilayers of a protein on a surface which are thicker than a monolayer, chemical linkers are used. For example, Tengvall et al, "Preparation of multilayer plasma protein films on silicon by EDC/NHS coupling chemistry," *Colloids and Surfaces B: Biointerfaces*, 28:261-272 (2003), disclose the use of ethyl-dimethyl-aminopropylcarbodiimide/N-hydroxy succinimide (EDC/NHS) compounds to link monolayers of fibrinogen, IgG, albumin, etc., on top of one another to form multilayer films. Multilayers of different proteins having specificity for each other, such as biotin and streptavidin, or protein and antibody, have also been used to build thicker films. Fibrinogen multilayer films built by use of EDC/NHS have been used for drug delivery in conjunction with bone implants and also for maintenance of soft tissue integrity when applied to suture threads. See, for example, the Aspenberg et al US Patent Publications Nos. 2006/0002970 and 2006/0003917. Skruvcoat and T-Coat from Optovent AB are examples of commercial products employing such films, referred to as FibMat films. Chemical linkers have also been used to bind a protein film or coating to a surface, i.e., an implant surface, as well as to link together the sequential layers constituting the protein film. Chemical substances such as glutaraldehyde (GA) and silane coupling agents, for example, aminopropyltriethoxy silane (APTES), have been used for such dual purposes and for substrate binding in combination with other chemical linkers used for multilayer film formation.

The use of chemical linkers, however, to form multilayer protein films and/or to bind multilayer protein films to a substrate creates several problems. First, the process of producing such multilayer films is a time-consuming multistep procedure. As an example, producing a fibrinogen multilayer coating using chemical linkers may take an average of 70 steps over a 2 day period, with more steps and time being required for thicker layers. Such processes clearly increase the cost of such layers in terms of both required materials and production time. Second, the use of chemical linkers introduces additional chemicals into an organism, i.e., the body, upon implantation, increasing risks of incompatibility and requiring further regulatory review and approval procedures. In fact, Sigma Aldrich, a supplier of glutaraldehyde, indicates that glutaraldehyde is toxic and environmentally dangerous, while EDC and APTES are generally considered corrosive. Further, since the chemical linkers can potentially chemically couple with a drug loaded into the film, possibly making a "new chemical entity" from a regulatory perspective, the use of multilayer films for drug delivery may be limited.

Attempts have also been made to physically manipulate proteins such as fibrinogen, lysozyme, and amyloid to form fibrils and fibers. For example, elongated proteins associate to form bands which in turn form fibrils, which are fibers of intertwined long proteins. Fibrils have been studied in order to attempt to understand protein interactions with (bio) material surfaces. See, for example, Cacciafesta et al, "Human plasma fibrinogen adsorption on ultraflat titanium oxide surfaces studied with atomic force microscopy," *Langmuir*, 16:8167-8175 (2000). More specifically, fibrils of fibrinogen have been used for production of Au-nanoparticles and for stimulation of hydroxyapatite growth in the design of biomaterial surfaces. However, the processes for forming such fibrils can take extended periods of time and/or require severe reaction conditions, for example, a low pH of around 2.

Accordingly, improved multilayer protein films and/or methods of making such films are desired.

SUMMARY OF THE INVENTION

It is therefore an object of the invention to provide improved multilayer protein films and methods of making the same.

In one embodiment, the invention is directed to a multilayer protein film having a mass of greater than 0.5 µg/cm$^2$, wherein the film consists essentially of protein. As will be discussed in greater detail below, the term "consisting essentially of" in the context of the inventive multilayer film means that the film is formed without and is free of non-therapeutic linking entities, i.e., non-therapeutic compounds or materials which are foreign to the human body and used to bind monolayers of protein to substrates, and/or to one another to form the multilayer film, and/or to a pharmaceutically active agent.

In another embodiment, the invention is directed to a drug delivery device which comprises a multilayer protein film according to the invention, and one or more pharmaceutically active agents loaded in the film.

In a further embodiment, the invention is directed to a biomedical implant which comprises an implant substrate and a multilayer protein film according to the invention on at least a portion of the implant substrate surface. Implant substrates of various materials and various configurations may be employed.

An additional embodiment of the invention is directed to a method of making a multilayer protein film having a mass of greater than 0.5 µg/cm$^2$, comprising contacting a substrate with a protein solution at a temperature that initiates an aggregation process at the substrate surface and at least in a volume corresponding to desired protein film thickness, wherein a multilayer protein film having a mass greater than 0.5 µg/cm$^2$ is formed on the substrate. The temperature for aggregation will be different for different proteins, but may typically be in the interval between 30° C. and 95° C.

The films, devices, biomedical implants and methods of the invention are advantageous in providing films which are free from non-therapeutic chemicals which are undesirable for in vivo applications such as implantation in the body, and/or in providing films which are easily made and avoid one or more time-consuming and/or laborious procedures of conventional techniques. Additional advantages and embodiments of the invention will be more fully apparent in view of the following detailed description.

DETAILED DESCRIPTION

In one aspect, the invention is directed to a multilayer protein film having a mass of greater than 0.5 µg/cm$^2$, wherein the film consists essentially of protein. As will be discussed in greater detail below, the term "consisting essentially of" in the context of the inventive multilayer film means that the film is formed without and is free of non-therapeutic linking entities, i.e., non-therapeutic compounds or materials which are foreign to the human body and used to bind monolayers of protein to substrates, and/or to one another to form the multilayer film, and/or to a pharmaceutically active agent. Thus, the multilayer protein film according to the invention is free of linking entities such as the conventionally employed EDC/NHS, APTES and glutaraldehyde linker materials. It must be understood however that the multilayer protein film defined as consisting essentially of protein may contain one or more pharmaceutically active agents, as discussed in detail below. In this regard, it will be appreciated that a pharmaceutically active agent may be loaded onto the film. The phrase "loaded onto" within the present disclosure is encompassing of "loaded on", "loaded into" and "loaded in" as well. The pharmaceutically active agent may be loaded onto the film by adsorption or absorption, wherein the agent is not part of the multilayer film structure, and/or such a pharmaceutically active agent may be loaded onto the multilayer film by bonding into the multilayer film. In either case, such a pharmaceutically active agent is employed for a therapeutic effect and is not merely employed as a linking entity. As such, the pharmaceutically active agent is dispersible or deliverable from the multilayer film, or acting in a catalytic fashion while still in the multilayer In one embodiment, wherein the pharmaceutically active agent is not bonded into the multilayer film, the multilayer film is homogeneous in composition throughout the film thickness to the extent that no linking entities are included therein; thus, there is no linking entities in the film composition at a substrate surface on which the film is formed or through the film to the film surface.

In another embodiment, a multilayer protein film according to the invention is provided on a substrate surface, one or more pharmaceutically active agents is loaded onto the multilayer film, and a second multilayer protein film according to the invention is provided on top of the first layer.

In one embodiment, the product comprises a substrate having a protein film on the surface and optionally a pharmaceutically active agent (a two-component system or more), that can be sold together but may be packaged separately.

A method of making the multilayer protein film comprises incubating the surface of a substrate by protein under conditions where the protein bind to the surface and aggregate in a volume at least corresponding to the desired thickness of the layer. In one embodiment, the method of making the multilayer protein film and loading of the pharmaceutically active agent onto the film comprises wet chemistry techniques, for example, but not limited to, incubation procedures in different solutions, or aerosol techniques, for example, but not limited to, aerosol spray, or combinations of said techniques.

The multilayer protein films of the invention have a thickness greater than that of monolayer films, preferably greater than 5 nm as measured by ellipsometry, or mass of greater than 0.5 µg/cm$^2$. In a specific embodiment, the multilayer protein films have a thickness as measured by mass of from 0.5 µg/cm$^2$ to about 50 g/cm$^2$, or have a thickness of from about 1 µg/cm$^2$ to about 50 g/cm$^2$, or from about 1 µg/cm$^2$ to about 30 µg/cm$^2$, or more specifically, from about 1 µg/cm$^2$ to about 15 µg/cm$^2$. In a further embodiment, the multilayer protein films have a thickness of from about 1 µg/cm$^2$ to about 10 µg/cm$^2$, or more specifically, from about 1.5 µg/cm$^2$ to about 5 µg/cm$^2$. In another embodiment, the multilayer protein films have a thickness of at least about 1 µg/cm$^2$, or, more specifically, at least about 1.2 µg/cm$^2$, or at least about 1.5 µg/cm$^2$.

The multilayer protein film may be formed of any suitable protein and one of ordinary skill in the art will appreciate that the protein will be selected depending on the desired use of the protein film. In various embodiments discussed herein, the protein film is used as a drug delivery device and/or as a surface coating for a biomedical implant. It should be appreciated however that the protein films as described herein have other uses as well, apparent in view of the present disclosure.

In one embodiment, the protein comprises a non-immunogenic protein or a human protein. Human proteins are, for example, disclosed in the Human Protein Reference Database (http://www.hprd.org). In a more specific embodiment, the protein comprises human blood protein, examples of which include, but are not limited to, fibrinogen, albumin, for example serum albumin, fibronectin, vitronectin, globulin, for example immunoglobulin (IgA, IgD, IgE, IgG, IgM), or a mixture of two or more thereof, tendon protein, for example of the Achilles tendon, or cartilage protein, for example, collagen, or a mixture of two or more of said proteins. In another embodiment, the protein comprises any composition of mentioned proteins, or more specific any fibrinogen composition with sufficient purity for actual application may be used. There are commercially available fibrinogen products that can be used, e.g. Haemocomplettan® (CSL Behring) containing a total amount of 1925-3010 mg powder, which consist of 900-1300 mg human fibrinogen, 400-700 mg human serum albumin and 200-350 mg NaCl. The protein can be purified from tissue, or produced by recombinant technology, for example expressed in cells, such as mammalian cells, bacteria, or phage, or synthesized in a machine. In a specific embodiment, the protein comprises a human blood protein, and in a more specific embodiment, the protein comprises fibrinogen, more specifically human fibrinogen. In further embodiments, the protein comprises fibrinogen and the multilayer protein film has a mass of from about 1 µg/cm$^2$ to about 15 µg/cm$^2$, or more specifically, from about 1.2 µg/cm$^2$ to about 15 µg/cm$^2$, or has a mass of at least 1 µg/cm$^2$, or, more specifically, at least 1.5 µg/cm$^2$. In another embodiment the source of protein may be human blood, in particular the patient's own blood. In a more specific embodiment, the protein comprises human blood plasma and/or human blood serum, which may be purified from the patient's own blood or from a different patient, or from a pool. It will be appreciated that multilayer films for veterinary use may employ respective animal proteins.

The multilayer protein film may be employed as a drug delivery device wherein the drug that is delivered may be the protein itself, for example, by resorption of the film. In a specific embodiment, the drug is an integrated part or fusion part of the protein forming the multilayer. For example, the protein may be a fusion protein with a structural portion and a pharmaceutically active portion linked with an enzymatically labile amino acid sequence. The drug is then delivered as the protein layers are degraded in vivo. Alternatively, one or more pharmaceutically active agents are loaded onto, e.g., by adsorption or absorption or bonding, the multilayer protein film for delivery in vivo.

Any of a wide variety of pharmaceutically active agents may be loaded onto the multilayer protein films of the present invention. In specific embodiments, the pharmaceutically active agent comprises an osteoactive drug, for example, but not limited to, bisphosphonate or strontium ranelate, growth factor, for example, but not limited to, bone morphogenic protein (BMP), fibroblast growth factor (FGB), insulin-like growth factor (IGF), epidermal growth factor (EGF), transforming growth factor (TGF) or platelet-derived growth factor (PDGF), matrix metallo proteinase inhibitor (MMP-inh), antibiotic (including antimicrobial compounds, including metallic compounds such as silver-containing or releasing compounds), or statin, or a mixture of two or more of said agents. In additional embodiments, the pharmaceutically active agent comprises one or more tetracyclines, chemically modified tetracyclines, synthetic matrix metalloproteinase inhibitors, including those of the hydroxamate subgroup, cyclooxygenase inhibitors, including cyclooxygenase 2 specific inhibitors; nuclear factor kappa B inhibitors; lipooxygenase inhibitors; corticosteroids, including glucocorticoids; macrolide antibiotics; hydroxymethylglutaryl coenzyme A reductase inhibitors (statins); angiotensin converting enzyme (ACE) inhibitors; angiotensin II receptor blockers (ARBs); aprotinin; gabexate mesilate; sulfasalazine; inhibitors of tumour necrosis factor alpha; and transforming growth factor beta inhibitors.

In a specific embodiment, the pharmaceutically active agent comprises a bisphosphonate. Various bisphosphonates are known in the art and suitable for use in loading the multilayer protein films of the invention, including, but not limited to zoledronic acid, ibandronate, risendronate, alendronate, etidronate, chlodronate, tiludronate, or pamidronate, or a mixture of two or more of said bisphosphonates.

In one embodiment of the invention, the multilayer protein film is formed on a substrate. As noted, the substrate may comprise a biomedical implant and the multilayer protein film is used to improve the function of the implant device and/or to deliver a drug to the area surrounding the implant. Biomedical implants are widely used in, e.g., orthopedics, dentistry, otology, and other bone and soft tissue environments, and include, but are not limited to orthopedic implants, sutures, cardiac implants, including catheters, stents, and valves, vessel prostheses, electronic devices, electrodes for deep brain stimulation, etc. The implant may be in the form of granules, for example of metal or ceramic granules, such as those employed in bone cement powders. In orthopedic and dental implants, the multilayer protein film may improve early stability, implant life time/prognosis, and/or functionality (such as early loading of dental implants or easy removal of implants, for example as compared to hydroxyapatite (HA)-coated implants). In soft tissue implants, the multilayer protein film may maintain tissue integrity, i.e. prevent tissue disintegration, in, for example, tendon such as Achilles tendon in order to heal sooner, or in colon anastomosis to prevent potentially mortal leakage. Further, the implant may be an inert material adapted solely for drug delivery in vivo. For example, the implant may comprise a porous material for use as a subcutaneous slow release of drug.

The substrate, for example, the biomedical implant substrate, may be formed of any suitable material, including, but not limited to, metals, e.g. titanium, or tantalum, alloys such as titanium alloys, stainless steel, and Co—Cr alloys, or ceramics, polymers, and polymer-metal composites.

The multilayer protein film may be provided on all or a portion of the substrate surface, as desired. The substrate surface may be treated prior to formation of the protein film thereon, if desired. For example, the substrate surface may be subjected to etching, plasma etching, priming, sand blasting, grinding, or the like. The resulting surface may have a nanostructured surface, for example with grooves, ridges, protuberances, hairs, needles, or the like. The invention is not limited by the substrate surface topology. The surface may be rough, porous, polished, etc. In one embodiment, a smooth implant surface may be etched or surface roughened before a protein film is applied. In one embodiment, the substrate surface is made more biocompatible prior to formation of the protein film by providing an inorganic film thereon, for example a hydroxyapatite film.

In the process of producing the multilayer protein film and/or loading of the pharmaceutically active agent, the aggregation conditions may be provided in different ways, particular by heating the protein to at least a temperature when aggregation is initiated and maintaining the temperature at or above that level for sufficient time for the film formation to a desired thickness to occur. For example, but not limited to, the solution may be pre-heated before adding the substrate, the substrate may be pre-heated before adding the solution, the substrate and the solution may both be pre-heated before added together, and/or the substrate and the solution may be mixed and heated together. The term solution in the above examples refers to the protein solution and/or to the pharmaceutically active agent solution.

In accordance with another aspect of the invention, a method of making a multilayer protein film having a mass greater than 0.5 µg/cm$^2$ comprises contacting a substrate with a protein solution at a temperature that initiates an aggregation-like state of the protein at the substrate surface and at least in a volume corresponding to desired protein film thickness, wherein a multilayer protein film having a mass greater than 0.5 µg/cm$^2$ is formed on the substrate. Typically an aqueous solution is employed. This step of incubating the substrate in the protein solution under the specified conditions surprisingly results in formation of a multilayer protein film. Without being limited by theory, it is believed that the protein is rendered sticky by the conditions of the solution, and the sticky proteins bind and/or crosslink with each other and with the surface in an indistinguishable process. It will therefore be evident that the present methods provide a significant improvement of the laborious and time consuming methods of the prior art. In a specific embodiment, standard cleaning procedures can be used to produce clean implant surfaces before application of the film by the incubating procedure. The clean implant is incubated in a protein solution.

By controlling the incubation parameters such as time, temperature, pH, ionic strength, cosolvents and protein composition, a film of the desired thickness is produced, as demonstrated in the Examples set forth herein. Thus, the incubation is suitably conducted at a temperature that initiates an aggregation process at the substrate surface and at least in a volume corresponding to desired protein film thickness, or specifically in a range of from about 30° C. to about 95° C., or more specifically, from about 30° C. to about 65° C. Further examples of temperature intervals are about 40° C. to about 60° C. (e.g. fibrinogen), about 60° C. to about 80° C. (e.g. albumin) and about 65° C. to about 85° C. (e.g. immunoglobulin). With addition of suitable compounds, film formation may be accomplished at lower temperatures, within the temperature range of liquid water. Advantageously, in specific embodiments, the incubation time may be up to about 72 hours, or from about momentaneous to about 72 hours, or from about 5 seconds to about 90 minutes, or from about 2 minutes to about 50 minutes, or from about 5 minutes to about 30 minutes, or from about 5 minutes to about 15 minutes. In more specific embodiments, these times are employed to form multilayer protein films having a mass greater than about 1 µg/cm$^2$.

The protein concentration in the solution may be varied and typically higher solution concentrations will result in thicker films. However, the concentration should not be so high as to prevent dissolution of the protein in the solution. In one embodiment, the protein solution comprises protein in an amount of from about 0.1 mg/ml to about 300 mg/ml, or more specifically from about 1 mg/ml to about 100 mg/ml, even more specifically from about 1 mg/ml to about 10 mg/ml. In another embodiment, the protein solution comprises protein in an amount of from about 1 mg/ml to about 5 mg/ml. The protein solution may be buffered and suitable buffers include, but are not limited to, acetate buffers, borate buffers, citrate buffers or phosphate buffers.

In a more specific embodiment, the protein solution is buffered with acetate buffer. The buffer pH is suitably in a range of pH 4-7, or more specifically in a range of pH 5-6. In one embodiment, the pH of the protein solution is around the isoelectric point (pI) of the protein, and, in a more specific embodiment, the pH of the protein solution is slightly below or above the protein pI, by, for example, 0.1-0.5 pH units. In one embodiment, the buffer concentration may typically be in a range of from about 0.1 mM to about 100 mM, or from about 1 mM to about 50 mM or, more specifically, from about 5 mM to about 30 mM. In further embodiments, the protein solution contains salt, for example, but not limited to, NaCl, and in a specific embodiment, has a concentration of from about 0.1% w/v to about 10% w/v, or more specifically from about 0.5% w/v to about 2% w/v. In one embodiment, the protein solution has a physiological salinity.

Preferably, the substrate surface is cleaned prior to incubation, mainly to remove organic material. Two methods for cleaning are mentioned, as exemplary only and are not intended to be limiting. In one embodiment, the substrate may be cleaned for five minutes in 70% ethanol in an ultrasonic bath and extensively rinsed in MilliQ® water before being ultrasonicated for five minutes in water. The substrate is finally rinsed in water and optionally dried in flowing nitrogen. Alternatively, the substrate may be incubated in an ultrasonic bath for five minutes in a solution containing 2% acetic acid and 2% triton X. The substrate is extensively rinsed in water and incubated in 70% ethanol in an ultrasonic bath, and extensively rinsed in water and ultrasonicated five minutes in water. The substrate is finally rinsed in water and optionally dried in flowing nitrogen.

In a contacting (incubation) step as described, a protein film of mass 1.2 µg/cm$^2$-1.5 µg/cm$^2$ may be easily formed, equaling about 20-25 nm when measured with ellipsometry. In specific embodiments, the multilayer protein film has a mass of at least 1.2 µg/cm$^2$ or at least 1.5 µg/cm$^2$. The contacting procedure can be repeated by incubating the implant substrate (containing the film formed in the first step) repeatedly, for a desired number of times, in protein solutions. In one embodiment, 1-10 incubations are conducted, while, in a more specific embodiment, 1-4 incubations are conducted. Optionally, fresh protein solutions can be employed in the second and/or subsequent incubation steps. Multilayer films of any thickness can be prepared and the films resulting from multiple incubation steps can be referred to as "multi-multilayer films" as multilayers are formed on top multilayers. Typically a 3-10 µg/cm$^2$ multilayer film (or "multi-multilayer film") can be easily formed by conducting the procedure as described three to four times, optionally using fresh protein solution in each contacting step. The thickness of this multi-multilayer film can be estimated to about 100 nm, although this thickness is outside the measuring range of ellipsometry.

When it is desired to load the multilayer protein film with a pharmaceutically active agent, the loading may be done during the film formation or in a subsequent step. To load the active agent during film formation, the active agent is included in the protein solution in the contacting step. If the active agent is loaded onto the film after film formation, the substrate, i.e., an implant substrate, with the film thereon is incubated in a solution containing the active agent, e.g. directly following film formation, or at any time point up till use of the implant. As discussed in detail above, the active agent may be loaded by adsorption or absorption, wherein the agent is non-covalently incorporated onto the protein film and retained by steric, hydrophobic, hydrogen bonding and/or electrostatic forces, or the agent may be bonded in the multilayer film.

The parameters suitable for loading the protein film with the pharmaceutically active agent will generally follow the following guidelines, although some variations may be appropriate depending on the specific features of a particular system. For example, the substrate with protein film can be contacted with a solution of the active agent at a temperature of from about 0° C. to about 95° C. and for a period of at least about momentaneous, more specifically from about 1 minute to about 72 hours. In a more specific embodiment, the contact period is from about 1 to about 60 minutes, or, more specifically, from about 5 to about 30 minutes. The concentration of the active agent in the solution will be dependent on the desired concentration of active agent in the protein film. In one embodiment, the solution has an active agent concentration in a range of from about 1 ng/ml to about 500 mg/ml, or from about 0.1 mg/ml to about 100 mg/ml, or from about 0.1 mg/ml to about 10 mg/ml or, more specifically, in a range of from about 0.1 mg/ml to about 5 mg/ml. The active agent solution may be buffered, for example in a pH range of 2-10, or more specifically in a range of pH 2-7, more specifically pH range of 3-5, or a range of 7-10, taking into account the pI of the protein of the film and the respective charges of the active agent and the protein. Suitable buffers include, but are not limited to, acetate buffers, borate buffers, citrate buffers or phosphate buffers. The buffer concentration may typically be in a range of from about 0.1 mM to about 20 mM, or more specifically from about 0.5 mM to about 10 mM. The amount of active agent loaded in the protein film is dependent on the film thickness and the parameters of the contacting step as described.

The amount of protein or active agent in the multilayer can be determined by different methods, for example the ellipsometry, HPLC, mass-spectrometry (for example ICP-SFMS), isotope label, or fluorescamine method. ICP-SFMS is a method used to quantify the different elements and isotopes in a sample. Detection of phosphorus may be used to quantify the amount of bisphosphonates absorbed into the protein film, sulphur may be used to quantify protein, if not present in the other components. Fluorescamine is a fluorophore that can be used to label proteins to quantify the total amount of protein in a sample. It is a simple method that allows small protein amounts down to nanograms to be measured. See Sogawa et al, *Journal of Biochemistry*, 83(6): 1783-1787 (1978), and Udenfriend, *Science*, 178(4063): 871-872 (1972).

In one embodiment of the invention, the method of making the protein film, with or without a pharmaceutically active agent, may be automated. The method may comprise a flow system with controlled parameters, such as, but not limited to, temperature, concentration, pH, flow velocity etc., making it possible to produce hundreds or thousands of coated substrates simultanesly.

After formation of the protein film on the substrate surface, optionally with an active agent loaded in the film, the substrate may be, rinsed, dipped or kept as is, before dried and packaged. A sterilization step may be employed as desired. According to one embodiment of the invention, for quality control of the coated parts, reference devices are coated in the same process and used for analysis of amounts of constituents.

Various embodiments of the invention are demonstrated in the following Examples.

General Experimental Procedures: In the following Examples, MilliQ® water is used for rinsing, diluting etc, and referred to as water. Incubations occurring in a laboratory environment, with a temperature range from about 16° C. to about 24° C., are referred to as room temperature. The fibrinogen is human plasminogen-depleted fibrinogen (Calbiochem, USA), the alendronate is alendronate monosodium trihydrate (LKT Laboratories, USA), and the $^{14}$C-labeled alendronate is from Larodan Fine Chemicals, Sweden. Pure titanium discs are ASTM B265 Grade 2 and with a surface area of 0.85 cm$^2$. Titanium surfaces are silicon wafers with a 2000 Å titanium layer, prepared by vapor deposition, used in parallel in the examples where thickness is measured by ellipsometry.

EXAMPLE 1

This example demonstrates the preparation of a titanium substrate with a multilayer film of fibrinogen (1.5 µg/cm$^2$) loaded with the bisphosphonate drug alendronate (0.16 µg/cm$^2$).

Pure titanium discs are cleaned for five minutes in a solution containing 2% acetic acid and 2% triton X. The substrate is extensively rinsed in water and incubated in 70% ethanol in an ultrasonic bath, and extensively rinsed in water and ultrasonicated five minutes in water. The substrate is finally rinsed in water and optionally dried in flowing nitrogen.

The discs are incubated in a 2 mg/ml solution of fibrinogen dissolved in 10 mM acetate buffer and 0.9% w/v NaCl, at pH 5.5. The incubation takes place in a 50° C. heating block for 10 minutes before the discs are rinsed in water and dried in flowing nitrogen. The resulting film mass is measured as approximately 1.5 µg/cm$^2$ with the fluorescamine method and approximately 25 nm with ellipsometry.

The titanium discs with the fibrinogen multilayer film are incubated in a 0.5 mg/ml alendronate solution, dissolved in 2.5 mM acetate buffer, at pH 4. The vials are placed on a rocking table and the incubation takes place at room temperature for 60 minutes. The discs are then rinsed in water and dried in flowing nitrogen. Approximately 0.16 µg/cm$^2$ alendronate in the film is detected by use of $^{14}$C-labeled alendronate.

EXAMPLE 2

This example demonstrates the preparation of a titanium substrate with a multilayer film of fibrinogen (1.5 µg/cm$^2$) loaded with the bisphosphonate drug zoledronic acid (0.18 µg/cm$^2$).

Pure titanium discs are cleaned as in Example 1, and a fibrinogen film is prepared as in Example 1. The fibrinogen-coated titanium discs are incubated in a solution of 0.5 mg/ml zoledronic acid (LKT Laboratories, USA), dissolved in 2.5 mM acetate buffer at pH 4. The incubation takes place under tilting at room temperature for 60 minutes, after which the surface is rinsed in water and dried in flowing nitrogen. Approximately 0.18 µg/cm$^2$ zoledronic acid was absorbed as measured by ICP-SFMS.

EXAMPLE 3

This example demonstrates the preparation of a titanium substrate with two multilayer films of fibrinogen (3.2 µg/cm$^2$) loaded with the bisphosphonate drug alendronate (0.3 µg/cm$^2$)

Pure titanium discs are cleaned as described in Example 1 and a first fibrinogen multilayer is prepared as in Example 1. The process for multilayer formation described in Example 1 is repeated, and the surfaces are rinsed and dried as described. Total mass of the fibrinogen multi-multilayer film is approximately 3.2 μg/cm².

The discs with the multi-multilayer film are loaded with alendronate according to the procedure described in Example 1, resulting in approximately 0.3 μg/cm² alendronate absorbed in the film as detected by use of $^{14}$C-labeled alendronate.

EXAMPLE 4

This example demonstrates the preparation of a stainless steel substrate with a multilayer fibrinogen film of 4 μg/cm² and loaded with 0.44 μg/cm² alendronate.

Stainless steel (SS) discs with a surface area of 0.85 cm² are used. The discs are cleaned as described in Example 1. The fibrinogen multilayer is prepared as in Example 1, resulting in approximately 4 μg/cm² fibrinogen with the fluorescamine method. The greater amount of fibrinogen on the SS discs as compared to the Ti-discs is due to a greater surface roughness.

The fibrinogen-coated stainless steel discs are loaded with alendronate according to the procedure described in Example 1, resulting in approximately 0.44 μg/cm² alendronate as detected by use of $^{14}$C-labeled alendronate.

EXAMPLE 5

This example demonstrates the preparation of a titanium substrate with a multilayer fibrinogen film (1.5 μg/cm²) and loaded with alendronate (0.16 μg/cm²) using a 5 minute incubation step.

The titanium discs are prepared with a fibrinogen multilayer film according to the procedure described in Example 1, except that the discs are not dried after rinsing in water. The discs are thereafter incubated in a 0.5 mg/ml solution of alendronate, dissolved in 2.5 mM acetate buffer, at pH 4, at room temperature for 5 minutes. The discs are rinsed in water and dried in flowing nitrogen. Approximately 0.16 μg/cm² alendronate in the film is detected by use of $^{14}$C-labeled alendronate.

EXAMPLE 6

This example demonstrates the preparation of a titanium substrate with a multilayer film of fibrinogen containing alendronate (0.12 μg/cm²) prepared in one combined fibrinogen and alendronate incubation.

The titanium discs are cleaned as in Example 1. The discs are incubated in a fibrinogen and alendronate solution containing 2 mg/ml fibrinogen and 0.5 mg/ml alendronate, dissolved in 10 mM acetate buffer and 0.9% w/v NaCl, at pH 4. The incubation takes place in a 50° C. heating block for 10 minutes before the surface is rinsed in water and dried in flowing nitrogen. Approximately 0.12 μg/cm² alendronate in the film is detected by use of $^{14}$C-labeled alendronate.

EXAMPLE 7

This example demonstrates the preparation of a titanium substrate with a multilayer film of fibrinogen prepared at an incubation temperature of 55° C.

The titanium surfaces are cleaned as in Example 1. The surfaces are incubated in a 2 mg/ml fibrinogen solution, dissolved in 10 mM acetate buffer and 0.9% w/v NaCl, at pH 5.5. The incubation takes place in a 55° C. heating block for 10 minutes before the surface is rinsed in water and dried in flowing nitrogen. Resulting film thickness is approximately 26 nm as measured with ellipsometry.

EXAMPLE 8

This example demonstrates the preparation of a titanium substrate with a multilayer film of fibrinogen (1.5 μg/cm²) loaded with a higher concentration of alendronate (2.3 μg/cm²).

The titanium discs are cleaned and the fibrinogen multilayer is prepared as in Example 1 except the discs are not dried after rinsing in water. The discs are thereafter incubated in a 5 mg/ml solution of alendronate, dissolved in 2.5 mM acetate buffer at pH 4, at room temperature for 5 minutes. The discs are rinsed in water and dried in flowing nitrogen. Approximately 2.3 μg/cm² alendronate in the film is detected by use of $^{14}$C-labeled alendronate.

EXAMPLE 9

This example demonstrates the preparation of a titanium substrate with a multilayer film of human serum albumin (HSA) (50 nm) loaded with the bisphosphonate drug alendronate (0.29 μg/cm²).

Pure titanium discs are cleaned as in Example 1. The discs are incubated in a 2 mg/ml solution of HSA (Sigma Aldrich, USA) dissolved in 10 mM acetate buffer and 3.0% w/v NaCl, at pH 5.3. The incubation takes place in a 70° C. heating block for 10 minutes before the discs are rinsed in water and dried in flowing nitrogen. The resulting film thickness is measured as approximately 50 nm with ellipsometry.

The titanium discs with the albumin multilayer film are incubated in a 0.5 mg/ml alendronate solution, dissolved in 2.5 mM acetate buffer, at pH 4. The discs are incubated at room temperature for 10 minutes, before the discs are rinsed in water and dried in flowing nitrogen. Approximately 0.29 μg/cm2 alendronate in the film is detected by use of $^{14}$C-labeled alendronate.

EXAMPLE 10

This example demonstrates the preparation of a titanium substrate with a multilayer film of immunoglobulin G (IgG) (40 nm) loaded with the bisphosphonate drug alendronate (0.29 μg/cm²).

Pure titanium discs are cleaned as in Example 1. The discs are incubated in a 2 mg/ml solution of IgG (Octapharma, Switzerland) dissolved in 10 mM acetate buffer and 1.2% w/v NaCl, at pH 4.3. The incubation takes place in a 75° C. heating block for 10 minutes before the surface is rinsed in water and dried in flowing nitrogen. The resulting film thickness is measured as approximately 40 nm with ellipsometry. The titanium discs with the IgG multilayer films are incubated in a 0.5 mg/ml alendronate solution dissolved in 2.5 mM acetate buffer, at pH 4. The discs are incubated at room temperature for 10 minutes, before the discs are rinsed in water and dried in flowing nitrogen. Approximately 0.29 μg/cm2 alendronate in the film is detected by use of $^{14}$C-labeled alendronate.

EXAMPLE 11

This example demonstrates the preparation of a titanium substrate with a multilayer film of fibrinogen (26 nm) loaded with the antibiotic gentamicin.

Pure titanium discs are cleaned as in Example 1. The discs are incubated in a 2 mg/ml solution of fibrinogen dissolved in 10 mM acetate buffer and 0.9% w/v HCl, at pH 5.3. The incubation takes place in a 50° C. heating block for 10 minutes before the discs are rinsed in water and dried in flowing nitrogen. The resulting film thickness is approximately 26 nm as measured with ellipsometry.

The titanium discs with the fibrinogen multilayer film are incubated in a 10 mg/ml solution of gentamicin (Sigma Aldrich, USA), dissolved in water, at room temperature for 60 minutes. The discs' antibacterial activity are then measured with diffusion susceptibility test, using agar plates with $10^8$ colony forming units per ml of *S. Aureus* (ATCC, USA). The discs release about 40 μg/cm$^2$ to about 80 μg/cm$^2$ gentamicin within the first 24 hours, and the inhibition zone is detectable up to 48 hours using serial plate transfer test.

EXAMPLE 12

This example demonstrates the preparation of a titanium substrate with a multi layer film of Haemocomplettan® (27 nm) loaded with the bisphosphonate drug alendronate (0.19 μg/cm$^2$).

Pure titanium discs are cleaned as in Example 1. The discs are incubated in a 2 mg/ml solution of Haemocomplettan® (CSL Behring, USA) dissolved in 10 mM acetate buffer and 0.9% w/v NaCI, at pH 5.5. The incubation takes place in a 50° C. heating block for 20 minutes before the discs are rinsed in water but not dried in flowing nitrogen. The resulting film thickness is measured as approximately 27 nm with ellipsometry.

The titanium discs with the Haemocomplettan® multilayer film are incubated in a 0.5 mg/ml alendronate solution, dissolved in 2.5 mM acetate buffer, at pH 4. The discs are incubated at room temperature for 5 minutes, before the discs are dipped in water and dried in flowing nitrogen. Approximately 0.19 μg/cm2 alendronate in the film is detected by use of $^{14}$C-labeled alendronate.

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

What is claimed is:

1. A biomedical implant, comprising:
    an implant substrate and
    a multilayer protein film on at least a portion of the implant substrate surface, wherein the implant substrate surface consists of one or more of titanium, titanium alloy, stainless steel, Co-Cr alloys, tantalum, or ceramics, produced by a method comprising:
    contacting the substrate with a protein human fibrinogen solution, and
    heating the protein fibrinogen solution to a temperature from about 30° C to 55° C sufficient to initiate protein aggregation at the substrate surface, thereby generating the multilayer protein film formed by aggregated protein on at least a portion of the implant surface,
    wherein:
        the multilayer protein fibrinogen film has a mass of greater than 0.5 μg/cm$^2$,
        the film consists essentially of protein,
        the film is formed without and is free of non-therapeutic linking entities,
        a pharmaceutically active agent that comprises a bisphosphonate is loaded onto the film,
        and
        the implant is a dental implant.

2. The biomedical implant of claim 1, wherein the film has a mass of from about 1 μg/cm$^2$ to about 30 μg/cm$^2$.

3. A biomedical implant, comprising an implant substrate, and a multilayer protein film having a thickness of from about 1 μg/cm$^2$ to about 15 μg/cm$^2$ on at least a portion of the implant substrate surface, wherein the implant substrate surface consists of one or more of titanium, titanium alloy, stainless steel, Co-Cr alloys, tantalum, or ceramics, and wherein the film consists essentially of human fibrinogen, wherein the film is aggregated protein, wherein the film is formed without and is free of non-therapeutic linking entities, wherein a bisphosphonate is loaded onto the film, and wherein the implant is a dental implant.

4. The biomedical implant of claim 1, wherein the pharmaceutically active agent is loaded onto the film by including the pharmaceutically active agent in the protein solution in the contacting step.

5. The biomedical implant of claim 1, wherein the pharmaceutically active agent is loaded onto the film after film formation by incubating the implant substrate with the film thereon in a solution containing the active agent.

6. The biomedical implant of claim 1, wherein the protein film has a thickness of at least 20 nm.

7. The biomedical implant of claim 1, wherein the method further comprises rinsing the obtained implant comprising the multilayer protein film.

8. The biomedical implant of claim 1, wherein the contacting and heating steps are repeated 1-10 times.

* * * * *